United States Patent
Rosso

(10) Patent No.: US 12,129,245 B2
(45) Date of Patent: Oct. 29, 2024

(54) CRYSTAL FORM OF 6-(CYCLOPROPAN-ECARBOXAMIDO)-4-((2-METHOXY-3-(1-METHYL-1H-1,2,4-TRIAZOL-3-YL)PHEN-YL)AMINO)-N-(METHYL-D$_3$) PYRIDAZINE-3-CARBOXAMIDE

(71) Applicant: Bristol-Myers Squibb Company, Princeton, NJ (US)

(72) Inventor: Victor W. Rosso, Monroe Township, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 261 days.

(21) Appl. No.: 17/587,374

(22) Filed: Jan. 28, 2022

(65) Prior Publication Data

US 2022/0259183 A1    Aug. 18, 2022

Related U.S. Application Data

(60) Provisional application No. 63/143,769, filed on Jan. 29, 2021.

(51) Int. Cl.
*C07D 403/12*    (2006.01)

(52) U.S. Cl.
CPC ........ *C07D 403/12* (2013.01); *C07B 2200/13* (2013.01)

(58) Field of Classification Search
CPC ......................... C07B 2200/13; C07D 403/12
See application file for complete search history.

(56) References Cited

U.S. PATENT DOCUMENTS

RE47,929 E    4/2020    Moslin et al.

FOREIGN PATENT DOCUMENTS

| WO | WO-2018/183656 A1 | 10/2018 | |
|---|---|---|---|
| WO | WO-2019232138 A1 * | 12/2019 | ........... A61K 31/501 |
| WO | WO-2020/251911 A1 | 12/2020 | |

OTHER PUBLICATIONS

International Search Report and Written Opinion for PCT/US2022/014261 dated Apr. 25, 2022.

* cited by examiner

*Primary Examiner* — John S Kenyon
*Assistant Examiner* — Rehana Ismail
(74) *Attorney, Agent, or Firm* — Covington & Burling LLP

(57) ABSTRACT

Disclosed is crystalline Form E of 6-(cyclopropanecarbox-amido)-4-((2-methoxy-3-(1-methyl-1H-1,2,4-triazol-3-yl) phenyl) amino)-N-(methyl-d$_3$)pyridazine-3-carboxamide. Form E is a neat crystalline form. Characterization data for Form E are disclosed.

18 Claims, 4 Drawing Sheets

CRYSTAL FORM OF 6-(CYCLOPROPANECARBOXAMIDO)-4-((2-METHOXY-3-(1-METHYL-1H-1,2,4-TRIAZOL-3-YL)PHENYL)AMINO)-N-(METHYL-D₃)PYRIDAZINE-3-CARBOXAMIDE

FIELD OF THE INVENTION

The present invention generally relates to a crystalline form of 6-(cyclopropanecarboxamido)-4-((2-methoxy-3-(1-methyl-1H-1,2,4-triazol-3-yl)phenyl)amino)-N-(methyl-d₃)pyridazine-3-carboxamide. The present invention also generally relates to pharmaceutical compositions comprising the crystalline form, as well methods for obtaining such crystalline form.

BACKGROUND OF THE INVENTION

The compound, 6-(cyclopropanecarboxamido)-4-((2-methoxy-3-(1-methyl-1H-1,2,4-triazol-3-yl)phenyl)amino)-N-(methyl-d₃)pyridazine-3-carboxamide, has the structure of Formula (I):

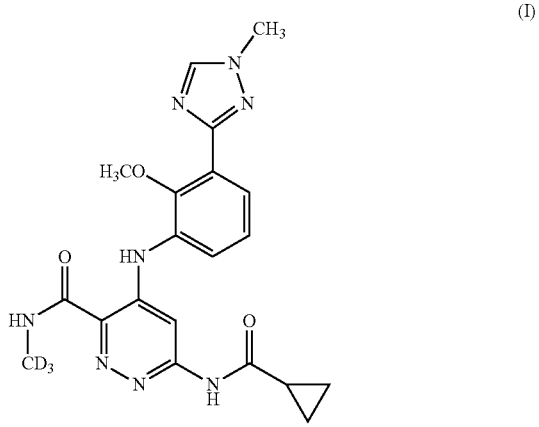 [SMILES: [2H]C([2H])([2H])NC(=O)c1nnc(NC(=O)C2CC2)cc1Nc1cccc(-c2ncn(C)n2)c1OC]

and is referred to herein as "Compound (I)". Compound (I) is disclosed in U.S. Pat. No. RE47,929 E, which is assigned to the present assignee. U.S. Pat. No. RE47,929 E also discloses methods of treatment employing Compound (I). Compound (I) is also known as Deucravacitinib.

Compound (I) is a Tyk2 inhibitor currently in clinical trials for the treatment of autoimmune and auto-inflammatory diseases such as psoriasis, psoriatic arthritis, lupus, lupus nephritis, Sjögren's syndrome, inflammatory bowel disease, Crohn's disease, and ankylosing spondylitis.

In the synthesis of a chemical compound intended for pharmaceutical use, it is necessary to isolate and purify the compound at the completion of the synthetic process and prior to further processing to provide the compound in a pharmaceutical formulation. The isolation and the purification steps, which can be combined or separate consecutive steps, provide the compound as a purified solid, ideally with minimal loss of yield during isolation of the compound from other components of the reaction mixture and/or during purification to remove impurities from the isolated compound sample.

It is desirable to provide a solid form of such a compound that can be reproducibly produced from the isolation and/or purification steps.

Further, it is desirable to isolate the compound in a solid form that is physically and chemically stable upon storage, including at different conditions of temperature and humidity. It is also advantageous to provide the compound in a solid form that exhibits little loss upon storage, and low moisture uptake.

It is also desirable to provide a compound in a solid form that is amenable to additional processing, for example a crystalline form that can be converted to other solid forms, such as an amorphous form or other crystalline forms.

As described herein, a crystalline form of Compound (I) surprisingly provides Compound (I) in a solid form that is physically and chemically stable at a range of storage conditions. This crystalline form also is surprisingly amenable to additional processing and can be converted to other solid forms. In addition, the crystalline form has sufficient solubility in solvents/solutions to permit preparation of other solid forms. The present invention is directed to these and other important aspects.

SUMMARY OF THE INVENTION

The present invention provides crystalline Form E of Compound (I). The name used herein to characterize a specific form, e.g. "Form E", should not be considered limiting with respect to any other substance possessing similar or identical physical and chemical characteristics, but rather it should be understood that this designation is a mere identifier that should be interpreted according to the characterization information also presented herein.

DETAILED DESCRIPTION OF THE INVENTION

Figure 1:
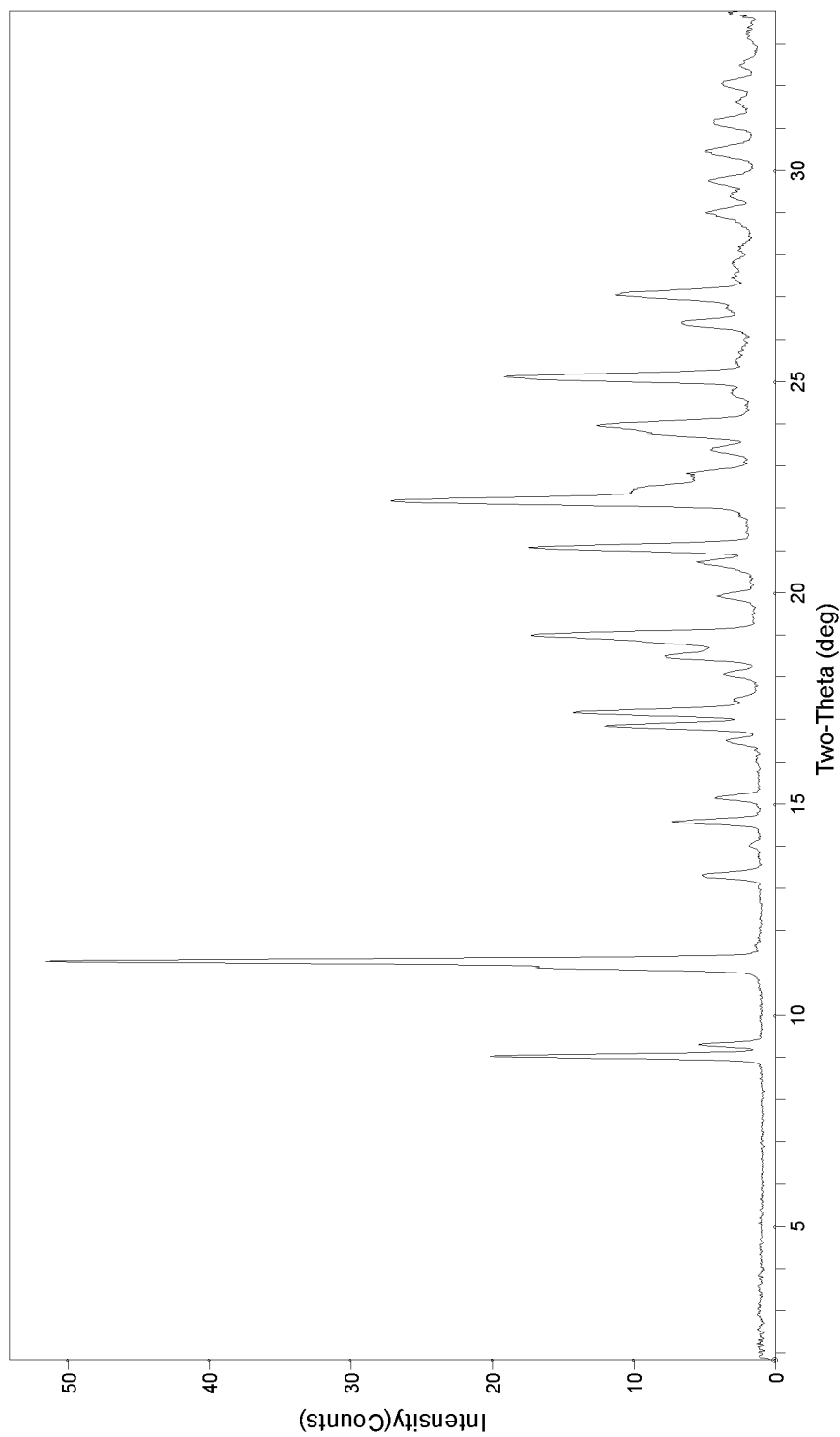
FIG. 1 shows the observed powdered X-ray diffraction pattern (CuKα at room temperature) of crystalline Form E of Compound (I).

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof.

The names used herein to characterize a specific form, e.g., "Form E" etc., are merely identifiers that are to be interpreted in accordance with the characterization information presented herein (or in references cited herein) and are not to be limited so as to exclude any other substance possessing similar or identical physical and chemical characteristics.

The definitions set forth herein take precedence over definitions set forth in any patent, patent application, and/or patent application publication incorporated herein by reference.

All numbers expressing quantities of ingredients, weight percentages, temperatures, and so forth that are preceded by the word "about" are to be understood as only approximations so that slight variations above and below the stated number may be used to achieve substantially the same results as the stated number. Accordingly, unless indicated to the contrary, numerical parameters preceded by the word "about" are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

All measurements are subject to experimental error, consistent with the spirit of the invention.

As used herein, "polymorphs" refer to crystalline forms having the same chemical structure but different spatial arrangements of the molecules and/or ions forming the crystals.

As used herein, "amorphous" refers to a solid form of a molecule and/or ion that is not crystalline. An amorphous solid does not display a definitive X-ray diffraction pattern with sharp maxima.

As used herein, "substantially pure," when used in reference to a crystalline form of a compound, means having the crystalline form at a purity greater than 90 weight %, including greater than 90, 91, 92, 93, 94, 95, 96, 97, 98, and 99 weight %, and also including equal to about 100 weight %, based on the weight of the sample or specimen. The remaining material comprises other form(s) of the compound, and/or reaction impurities and/or processing impurities arising from its preparation. For example, a crystalline form of Compound (I) may be deemed substantially pure in that it has a purity greater than 90 weight %, as measured by means that are at this time known and generally accepted in the art, where the remaining less than 10 weight % of material comprises amorphous and/or other form(s) of Compound (I) and/or reaction impurities and/or processing impurities.

As used herein, a powder X-ray diffraction (PXRD) pattern "comprising" a number of peaks selected from a specified group of peaks, is intended to include PXRD patterns having additional peaks that are not included in the specified group of peaks. For example, a PXRD pattern comprising four or more, preferably five or more, 2θ values selected from: a, b, c, d, e, f, g, and h, is intended to include a PXRD pattern having: (a) four or more, preferably five or more, 2θ values selected from: a, b, c, d, e, f, g, and h; and (b) zero or more peaks that are not one of peaks a, b, c, d, e, f, g, and h.

The presence of reaction impurities and/or processing impurities may be determined by analytical techniques known in the art, such as, for example, chromatography, nuclear magnetic resonance spectroscopy, mass spectrometry, and/or infrared spectroscopy.

As used herein, the unit cell parameter "molecules per unit cell" refers to the number of molecules of Compound (I) in the unit cell.

Forms of Compound (I) have been described in WO 2018/183656 (Form A), WO 2019/232138 (Form B), and WO 2020/251911 (Forms C and D). The present invention generally relates to Form E of Compound (I).

Form E of Compound (I)

In some embodiments, Compound (I) is provided as a crystalline material comprising Form E. The crystalline Form E of Compound (I) is a neat crystalline form.

In certain embodiments, crystalline Form E of Compound (I) is characterized by unit cell parameters approximately equal to the following:

Cell dimensions:
  a=10.41±0.10 Å
  b=12.65±0.10 Å
  c=15.70±0.10 Å
  α=90.0°
  β=103.5±1.0°
  γ=90.0°
Space group: P2$_1$/n
Molecules per unit cell (Z): 4
Unit cell volume=2011±20 Å$^3$
Density (calculated)=1.406 g/cm$^3$, wherein the unit cell parameters of Form E of Compound (I) are measured at a temperature of about 100 K.

TABLE 1

Form E of Compound (I)
Characteristic PXRD 2θ values (CuKα)

| | | | | | | |
|---|---|---|---|---|---|---|
| 9.0 ± 0.2° | 9.3 ± 0.2° | 11.3 ± 0.2° | 13.3 ± 0.2° | 14.0 ± 0.2° | 14.6 ± 0.2° | 15.2 ± 0.2° |
| 16.5 ± 0.2° | 16.9 ± 0.2° | 17.2 ± 0.2° | 17.5 ± 0.2° | 18.1 ± 0.2° | 18.5 ± 0.2° | 19.0 ± 0.2° |
| 19.9 ± 0.2° | 20.7 ± 0.2° | 21.1 ± 0.2° | 22.2 ± 0.2° | 22.5 ± 0.2° | 22.8 ± 0.2° | 23.4 ± 0.2° |
| 23.8 ± 0.2° | 24.0 ± 0.2° | 24.8 ± 0.2° | 25.1 ± 0.2° | 25.4 ± 0.2° | 25.7 ± 0.2° | 26.4 ± 0.2° |
| 26.8 ± 0.2° | 27.0 ± 0.2° | 27.5 ± 0.2° | 27.8 ± 0.2° | 28.2 ± 0.2° | 29.0 ± 0.2° | 29.4 ± 0.2° |
| 29.7 ± 0.2° | 30.4 ± 0.2° | 31.1 ± 0.2° | 31.7 ± 0.2° | 32.0 ± 0.2° | 32.5 ± 0.2° | 33.2 ± 0.2° |
| 33.8 ± 0.2° | 34.5 ± 0.2° | 34.9 ± 0.2° | 35.9 ± 0.2° | — | — | — |

In some embodiments, crystalline Form E of Compound (I) is characterized by a powder X-ray diffraction (PXRD) pattern comprising two or more 2θ values in degrees (CuKα) selected from: 9.0±0.2, 11.3±0.2, 15.2±0.2, and 21.1±0.2, wherein the PXRD pattern of Form E is measured at room temperature.

In certain embodiments, crystalline Form E of Compound (I) is characterized by a powder X-ray diffraction pattern comprising 2θ values in degrees (CuKα) at 9.0±0.2 and 11.3±0.2, wherein the PXRD pattern of Form E is measured at room temperature.

In further embodiments, crystalline Form E of Compound (I) is characterized by a powder X-ray diffraction pattern comprising 2θ values in degrees (CuKα) at 9.0±0.2, 11.3±0.2, 15.2±0.2, and 21.1±0.2, wherein the PXRD pattern of Form E is measured at room temperature.

In certain embodiments, crystalline Form E of Compound (I) is characterized by (i) a powder X-ray diffraction pattern comprising 2θ values in degrees (CuKα) at 9.0±0.2 and 11.3±0.2, wherein the PXRD pattern of Form E is measured at room temperature; and (ii) an endotherm with peak max in the approximate range of from 249° C. to 253° C. In further embodiments, the endotherm peak max is at about 251° C. It should be understood that, in some cases, the endothermic event may not be detected.

In certain embodiments, crystalline Form E of Compound (I) is characterized by (i) a powder X-ray diffraction pattern comprising 2θ values in degrees (CuKα) at 9.0±0.2, 11.3±0.2, 15.2±0.2, and 21.1±0.2, wherein the PXRD pattern of Form E is measured at room temperature; and (ii) an endotherm with peak max in the approximate range of from 249° C. to 253° C. In further embodiments, the endotherm peak max is at about 251° C.

In certain embodiments, crystalline Form E of Compound (I) is characterized by an observed powder X-ray diffraction pattern substantially as shown in FIG. 1.

In some embodiments, crystalline Form E of Compound (I) is characterized by an endotherm peak max in the approximate range of from 249° C. to 253° C. In further embodiments, the endotherm peak max is at about 251° C.

Figure 2:
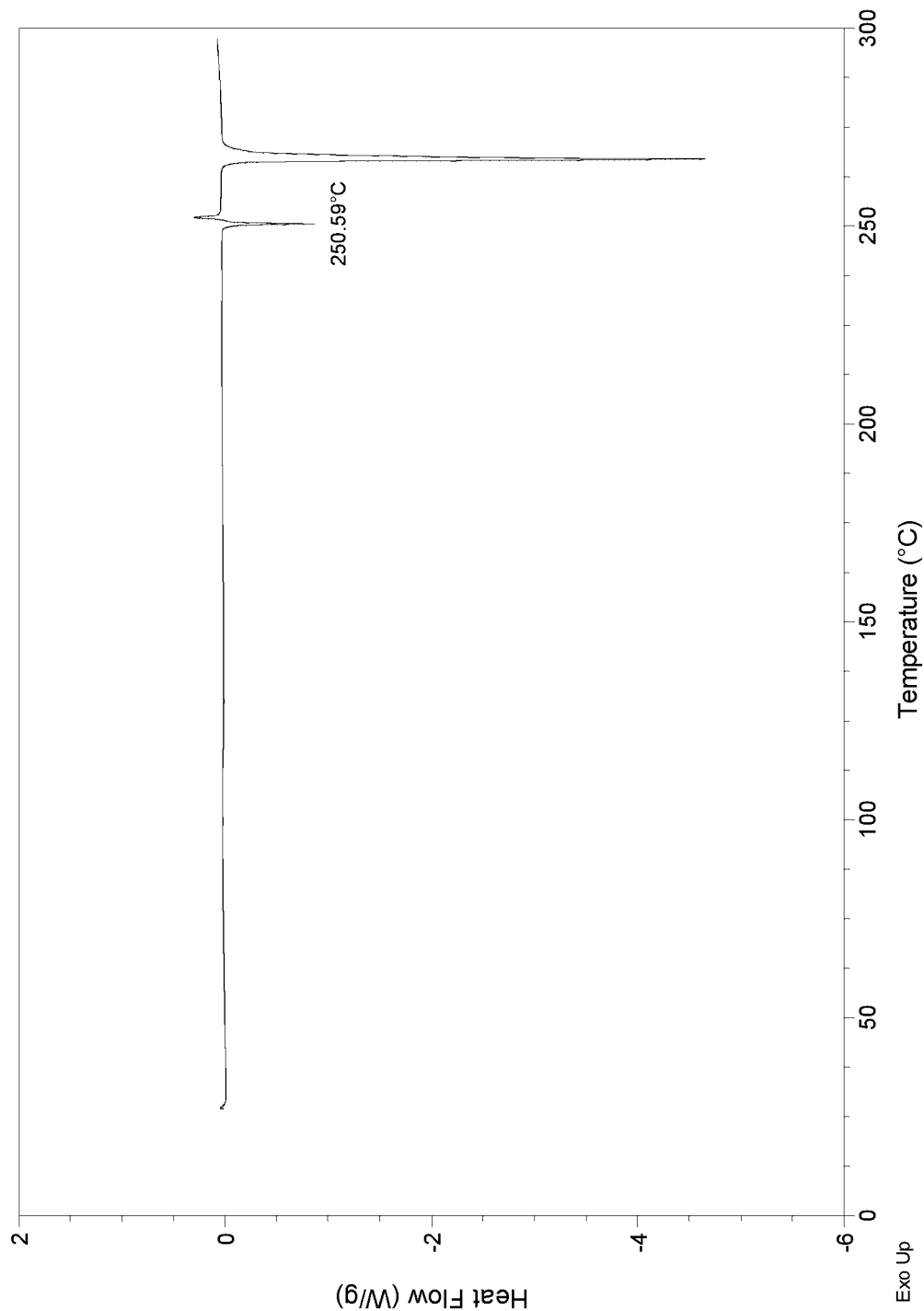
FIG. 2 shows a differential scanning calorimetry (DSC) thermogram of crystalline Form E of Compound (I).

In some embodiments, crystalline Form E of Compound (I) is characterized by a differential scanning calorimetry (DSC) thermogram substantially in accordance with the thermogram shown in FIG. 2.

In certain embodiments, crystalline Form E of Compound (I) is characterized by (i) a powder X-ray diffraction pattern comprising the 2θ values in degrees (CuKα) at 9.0±0.2 and 11.3±0.2, measured at room temperature; and (ii) a differential scanning calorimetry (DSC) thermogram substantially in accordance with the thermogram shown in FIG. 2.

In some embodiments, crystalline Form E of Compound (I) is characterized by a thermogravimetric analysis (TGA) thermogram having weight loss of less than 0.1% upon being heated to a temperature of about 150° C. In certain embodiments, crystalline Form E of Compound (I) is characterized by a thermogravimetric analysis (TGA) thermogram having weight loss of less than 0.1% upon being heated to a temperature of about 175° C. In further embodiments, crystalline Form E of Compound (I) is characterized by a thermogravimetric analysis (TGA) thermogram showing less than 0.5% weight loss at about 200° C.

Figure 3:
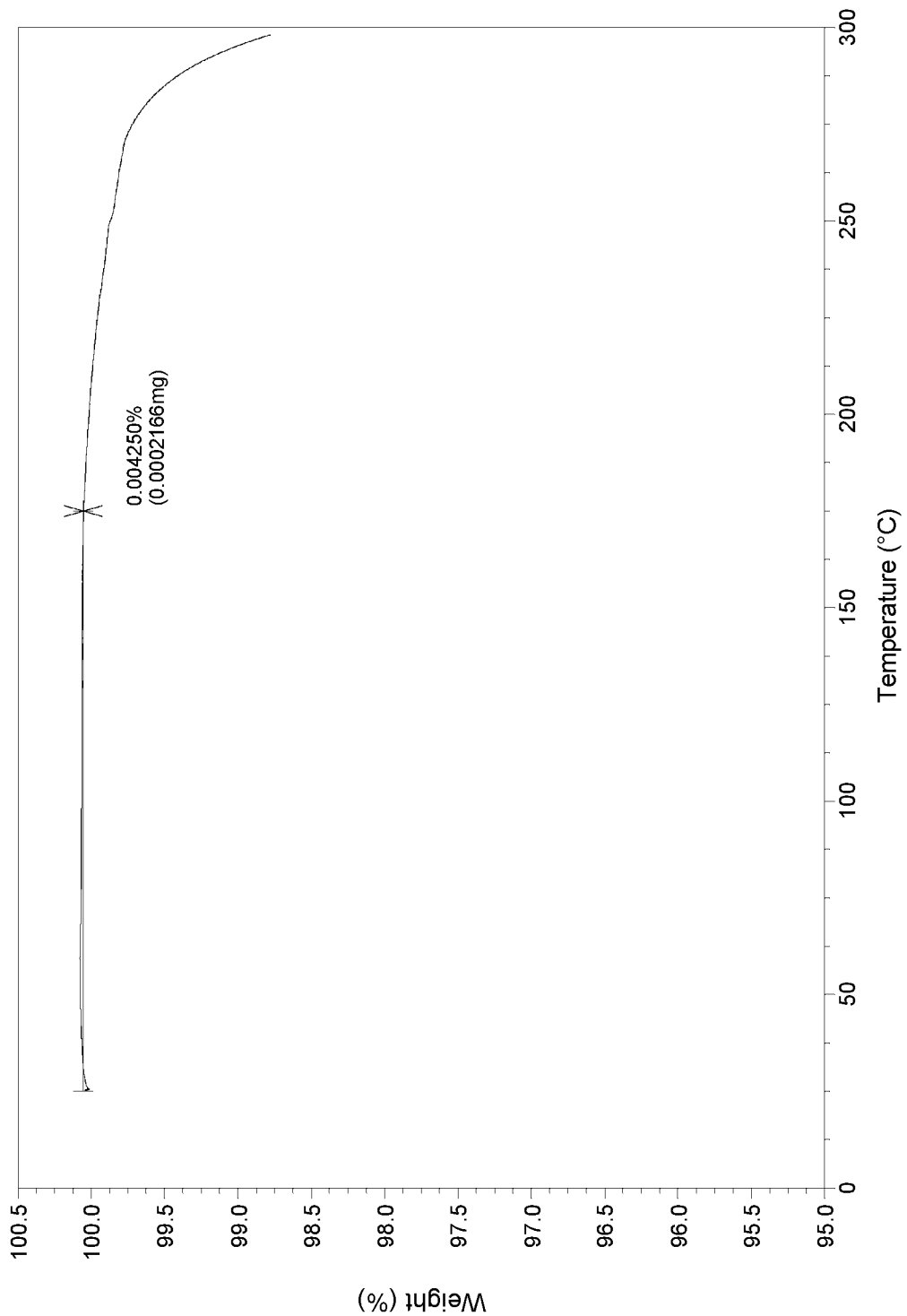
FIG. 3 shows a thermogravimetric analysis (TGA) thermogram of Form E of Compound (I).

In certain embodiments, crystalline Form E of Compound (I) exhibits a thermogravimetric analysis (TGA) thermogram substantially as shown in FIG. 3.

Figure 4:
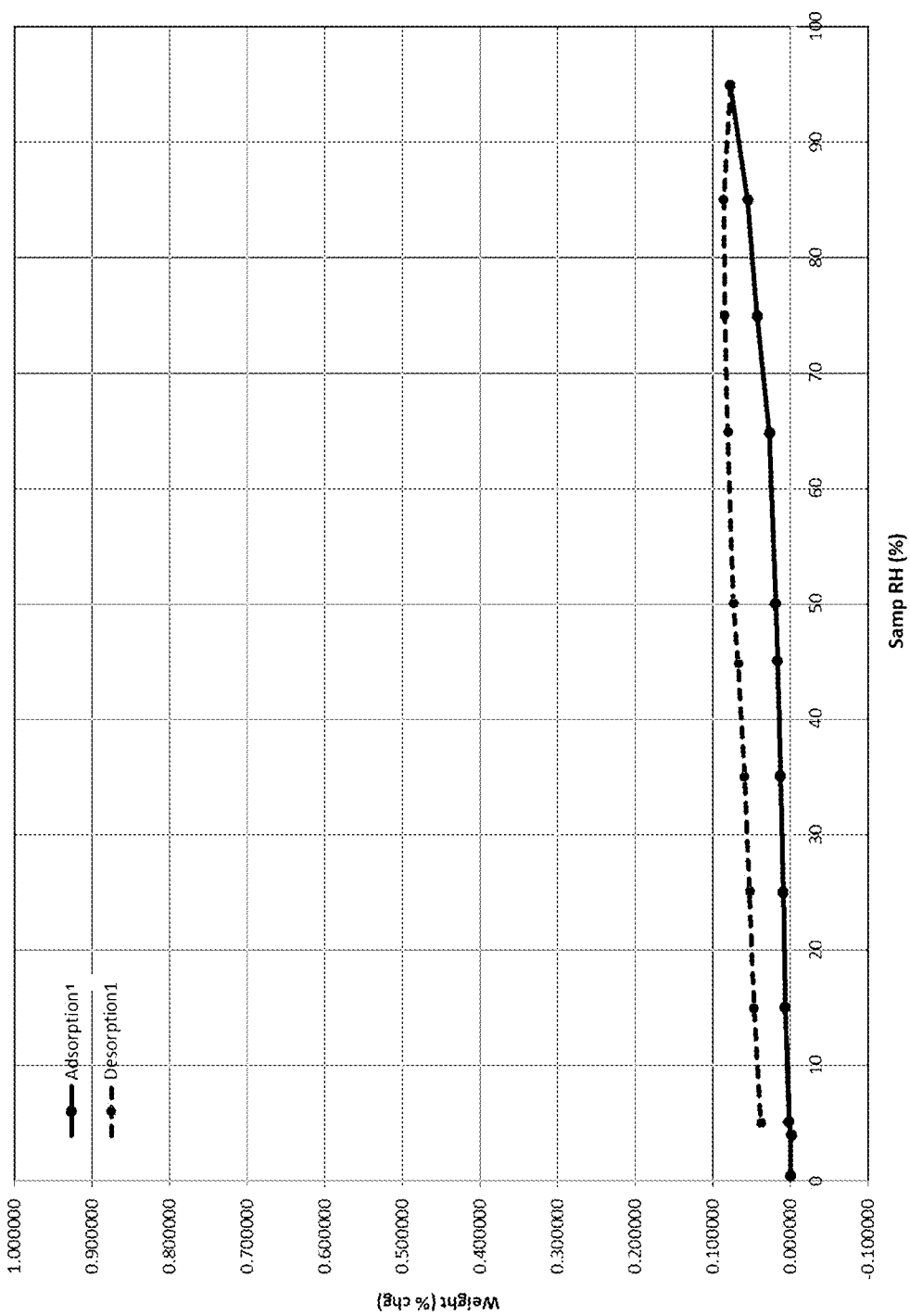
FIG. 4 shows moisture-sorption isotherms for Form E of Compound (I) measured at 25° C.

In certain embodiments, crystalline Form E of Compound (I) exhibits a moisture-sorption isotherm substantially as shown in FIG. 4.

In some embodiments, the Form E of Compound (I) is substantially pure. For example, Form E of Compound (I) may be present in a sample at a purity of greater than 90 weight %, greater than 95 weight %, or greater than 99 weight %, while the remaining material comprises other form(s) of the compound and/or reaction impurities and/or processing impurities.

In certain embodiments, the crystalline form of Compound (I) consists essentially of Form E. For such embodiments, crystalline Compound (I) may comprise at least about 90 weight %, preferably at least about 95 weight %, and more preferably at least about 99 weight %, of crystalline Form E, based on the weight of Compound (I).

Certain embodiments also provide a composition comprising 6-(cyclopropanecarboxamido)-4-((2-methoxy-3-(1-methyl-1H-1,2,4-triazol-3-yl)phenyl) amino)-N-(methyl-d₃) pyridazine-3-carboxamide, wherein at least 95 weight %, preferably at least 97 weight %, and more preferably at least 99 weight % of said 6-(cyclopropanecarboxamido)-4-((2-methoxy-3-(1-methyl-1H-1,2,4-triazol-3-yl)phenyl)amino)-N-(methyl-d₃)pyridazine-3-carboxamide is in crystalline Form E.

In further embodiments, a pharmaceutical composition is provided comprising Form E of Compound (I), and at least one pharmaceutically-acceptable carrier and/or diluent.

In certain embodiments, a pharmaceutical composition comprises substantially pure Form E of Compound (I), and at least one pharmaceutically-acceptable carrier and/or diluent.

In certain embodiments, Form E of Compound (I) is combined with at least one pharmaceutically acceptable carrier and/or diluent to provide at least one pharmaceutical composition.

In some embodiments, a pharmaceutical composition comprises Form E of Compound (I) and other solid forms of Compound (I). Such other solid forms can be, for example, other crystalline forms (e.g., Form A) and/or amorphous Compound (I).

Crystalline forms may be prepared by a variety of methods, including for example, crystallization or recrystallization from a suitable solvent, sublimation, growth from a melt, solid state transformation from another phase, crystallization from a supercritical fluid, and jet spraying. Techniques for crystallization or recrystallization of crystalline forms from a solvent mixture include, for example, evaporation of the solvent, decreasing the temperature of the solvent mixture, crystal seeding a supersaturated solvent mixture of the molecule and/or salt, freeze drying the solvent mixture, and addition of antisolvents (countersolvents) to the solvent mixture. High throughput crystallization techniques may be employed to prepare crystalline forms including polymorphs.

Crystals of drugs, including polymorphs, methods of preparation, and characterization of drug crystals are discussed in *Solid-State Chemistry of Drugs*, S. R. Byrn, R. R. Pfeiffer, and J. G. Stowell, 2$^{nd}$ Edition, SSCI, West Lafayette, Indiana (1999).

For crystallization techniques that employ solvent, the choice of solvent or solvents typically depends on one or more factors, such as solubility of the compound, crystallization technique, and vapor pressure of the solvent. Combinations of solvents may be employed, for example, the compound may be solubilized into a first solvent to afford a solution, followed by the addition of an antisolvent to decrease the solubility of the compound in the solution and to afford the formation of crystals. An antisolvent is a solvent in which the compound has low solubility.

In one method to prepare crystals, a compound is suspended and/or stirred in a suitable solvent to afford a slurry, which may be heated to promote dissolution. The term "slurry", as used herein, means a saturated solution of the compound, which may also contain an additional amount of the compound to afford a heterogeneous mixture of the compound and a solvent at a given temperature.

Seed crystals may be added to any crystallization mixture to promote crystallization. Seeding may be employed to control growth of a particular polymorph or to control the particle size distribution of the crystalline product. Accordingly, calculation of the amount of seeds needed depends on the size of the seed available and the desired size of an average product particle as described, for example, in "Programmed Cooling of Batch Crystallizers," J. W. Mullin and J. Nyvlt, *Chemical Engineering Science,* 1971, 26, 369-377. In general, seeds of small size are needed to effectively control the growth of crystals in the batch. Seeds of small size may be generated by sieving, milling, or micronizing of large crystals, or by micro-crystallization of solutions. Care should be taken that milling or micronizing of crystals does not result in any change in crystallinity from the desired crystal form (i.e., a change to amorphous or to another polymorph).

A cooled crystallization mixture may be filtered under vacuum, and the isolated solids may be washed with a suitable solvent, such as cold recrystallization solvent, and dried under a nitrogen purge to afford the desired crystalline form. The isolated solids may be analyzed by one or more suitable spectroscopic or analytical techniques, such as solid state nuclear magnetic resonance, differential scanning calorimetry, X-ray powder diffraction, or the like, to assess formation of the preferred crystalline form of the product. The resulting crystalline form is typically produced in an amount of greater than about 70 weight % isolated yield, preferably greater than 90 weight % isolated yield, based on the weight of the compound originally employed in the crystallization procedure. The product may be co-milled or passed through a mesh screen to delump the product, if necessary.

Crystalline forms may be prepared directly from the reaction medium of the final process for preparing Compound (I). Such preparation may be achieved, for example, by employing in the final process step a solvent or a mixture of solvents from which Compound (I) may be crystallized. Alternatively, crystalline forms may be obtained by distillation or solvent addition techniques. Suitable solvents for this purpose include, for example, the aforementioned nonpolar solvents and polar solvents, including protic polar solvents such as alcohols, and aprotic polar solvents such as ketones.

The presence of more than one polymorph in a sample may be determined by techniques such as powder X-ray diffraction (PXRD) or solid state nuclear magnetic resonance spectroscopy (ssNMR). For example, the presence of extra peaks in the comparison of an experimentally measured PXRD pattern with a simulated PXRD pattern may indicate the presence of more than one polymorph in the sample. The simulated PXRD may be calculated from single crystal X-ray data. See Smith, D. K., "*A FORTRAN Program for Calculating X-Ray Powder Diffraction Patterns*," Lawrence Radiation Laboratory, Livermore, California, UCRL-7196 (April 1963).

Form E of Compound (I) may be characterized using various techniques, the operation of which are well known to those of ordinary skill in the art. Form E may be characterized and distinguished using single crystal X-ray diffraction, which is based on unit cell measurements of a single crystal at a fixed analytical temperature. A detailed description of unit cells is provided in Stout & Jensen, X-Ray Structure Determination: A Practical Guide, Macmillan Co., New York (1968), Chapter 3, which is herein incorporated by reference. Alternatively, the unique arrangement of atoms in spatial relation within the crystalline lattice may be characterized according to the observed fractional atomic coordinates. Another means of characterizing the crystalline structure is by powder X-ray diffraction analysis in which the diffraction profile is compared to a simulated profile representing pure powder material, both run at the same analytical temperature, and measurements for the subject form are characterized as a series of 2θ values (e.g., two, three, four or more).

Other methods of characterizing the form may be used. Such methods include solid state nuclear magnetic resonance (ssNMR), differential scanning calorimetry (DSC), thermography, and gross examination of the crystalline or amorphous morphology. Two or more of these parameters may also be used in combination to characterize the subject form.

Utility

Crystalline Form E of Compound (I) can be used to isolate Compound (I) from other components at the completion of the synthesis process; and/or to purify Compound (I) by one or a series of crystallization steps. The isolation and the purification steps can be combined or practiced as separate process steps. Crystalline Form E can also be used to make other solid forms of Compound (I), including, for example, Form A, which is described in WO 2018/183656, and/or amorphous Compound (I). In certain embodiments, a method of preparing amorphous Compound (I) comprises preparing crystalline Form E, wherein crystalline Form E is characterized as described herein. In further embodiments, such amorphous Compound (I) is then used to make a dosage form (e.g., a dosage form comprising a solid dispersion of amorphous Compound (I)) for clinical use.

Crystalline Form E of Compound (I) may be used alone or in combination with other forms of Compound (I), and/or formulated with one or more excipients or other active pharmaceutical ingredients to make pharmaceutical compositions.

EXAMPLES

The invention will now be further described by the following working example(s), which are preferred embodiments of the invention. All temperatures are in degrees Celsius (° C.) unless otherwise indicated. These examples are illustrative rather than limiting and it is to be understood that there may be other embodiments that fall within the spirit and scope of the invention.

For ease of reference, the following abbreviations may be used herein.

Abbreviations

ACN or MeCN acetonitrile
AP area percent
DBU 1,8-diazabicyclo[5.4.0]undec-7-ene
DIPEA N,N-diisopropylethylamine (Hunig's base)
EDC HCl 1-(dimethylaminopropyl)-3-ethylcarbodiimide hydrochloride
equiv. molar equivalents
Et ethyl
H hour(s)
HOBt 1-hydroxy benzotriazole
IPA isopropyl alcohol
min minute(s)
Me methyl
MTBE methyl tert-butyl ether
NMP n-methylpyrrolidone
Pd/C palladium on carbon
THF tetrahydrofuran
TsCl p-toluenesulfonyl chloride Example 1: Preparation of Crystalline Form E of Compound (I)

Approximately 33 mg of Compound (I) were dissolved in 0.16 mL of NMP at 90° C. in a 1 mL vial. The vial was placed in a 100° C. reactor block and 0.8 mL of 1,4 Dioxane was added. The vial was continuously stirred overnight at 80° C. The vial was then allowed to cool to ambient temperature and then stirred over the following two days. Isolated samples for PXRD exhibited the Form E pattern.

Example 2: Preparation of Crystalline Form E of Compound (I)

200 mg of Compound (I) were placed in 0.8 mL of NMP, and then heated to dissolve in a block set at 90° C. After cooling to room temperature, 3 mL of 1,4 Dioxane was added. Seeding was done with remnants of slurry from the prior experiment (Example 1). An additional 4 mL of Dioxane was added, and the mixture was stirred overnight at ambient temperature, whereupon crystals had formed. Crystals were isolated by filtration, washed with excess MTBE (to deliquor NMP/Dioxane), and dried overnight at ambient temperature under 25 inches of vacuum. Dry powder exhibited the Form E PXRD pattern.

Example 3: Preparation of Crystalline Form E of Compound (I)

Compound (I) (~2 g) was dissolved in 36 g 1-BuOH:water 80:20 wt % at 75° C. for ~20-30 minutes until a clear solution was obtained. The solution was hot filtered in a pre-warmed flask; the flask was then capped and placed in a freezer overnight, resulting in a white precipitate that consumed all of the liquid phase (thick suspension). The suspension was stored in the freezer for ~4 months. The thick suspension was then transferred on a paper filter for vacuum filtration. The resulting wet cake was washed twice with 10 mL of acetone:water 70:30 wt %. Approximately 5.78 g wet solid was then slurried in 21 mL of acetone:water 70:30 wt %. The resulting suspension was subjected to temperature cycling: 3 cycles (5-45-5° C.); 2 cycles (5-35-5° C.); 1 cycle (10-35-10° C.), ending in a last hold at 10° C. for 6 hours. Solids of the suspension were isolated by vacuum filtration, washed twice with 5 mL of acetone:water 70:30 wt %. The solids were exposed to 84% RH for 1 day. A small portion was analyzed by PXRD and the solids were consistent with Form E. Thereafter, the sample was vacuum dried at 42° C. for 1 day and re-analyzed. The solids again were consistent with Form E.

Synthesis of 6-(cyclopropanecarboxamido)-4-((2-methoxy-3-(1-methyl-1H-L2,4-triazol-3-yl)phenyl)amino)-N-(methyl-d$_3$)pyridazine-3-carboxamide Step 1: Preparation of Compound 2

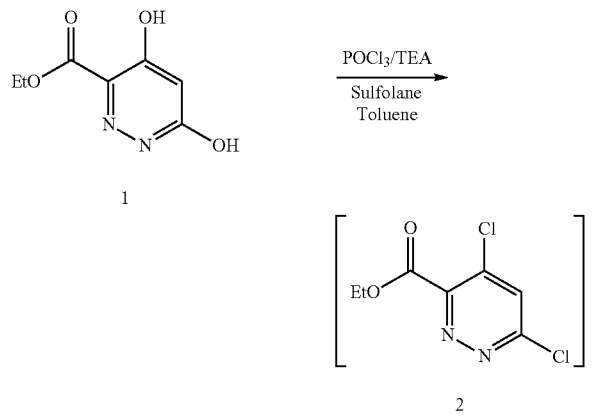

To a glass lined reactor were charged toluene (0.26 kg), sulfolane (3.4 kg), Compound 1 (1.0 kg) and POCl$_3$ (2.7 kg). The crude was cooled to 0° C. Triethylamine (0.89 kg) was charged, and the resulting crude mixture was heated to 65° C. and aged till the reaction reached completion. The reaction mass was cooled to 5° C.

In a separate reactor, water (7.5 kg) was charged and cooled to 5° C. The reaction mass was added slowly to the water solution, maintaining the internal temperature below 5° C. Additional water (0.5 kg) was used to rinse the reactor and aid the transfer. The resulting mixture was agitated at 5° C. for 3 hours, then extracted with MTBE three times (3×4.5 kg). The combined organic layers were washed sequentially with aqueous pH 7 buffer solution (5.0 L/kg, 15 wt % KH$_2$PO$_4$/K$_2$HPO$_4$) and water (2.5 kg). The crude was distilled under vacuum until total volume became approximately 3 L/kg. ACN (2×6.3 kg) was added followed by additional distillations back to ~3 L/kg. The crude was cooled to 20° C. to afford Compound 2 as a 30-36 wt % solution in 90-95% yield.

Step 2: Preparation of Compound 3

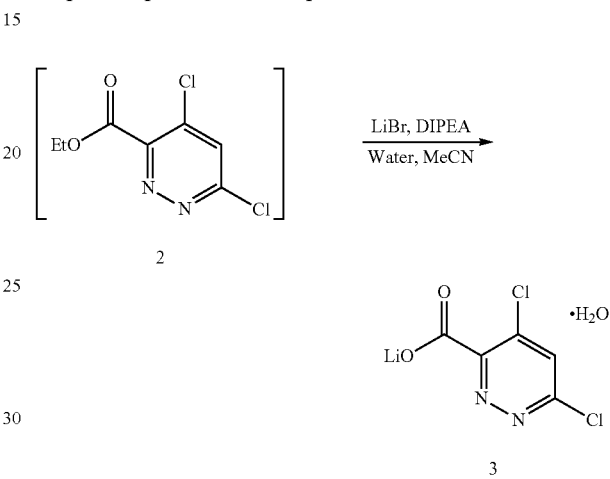

ACN (2.7 kg), lithium bromide (1.18 kg) and water (0.65 kg) were charged to a glass-lined reactor at 25° C. Compound 2 crude solution prepared above (limiting reagent) was added, followed by DIPEA (1.82 kg). The resulting slurry was agitated at 25° C. until the reaction reached completion. The product was isolated by filtration. The crude solid was washed with ACN (1.6 kg). The cake was dried under vacuum at 45° C. Compound 3 was isolated in 98 AP and 83% yield.

Step 3: Preparation of Compound 8

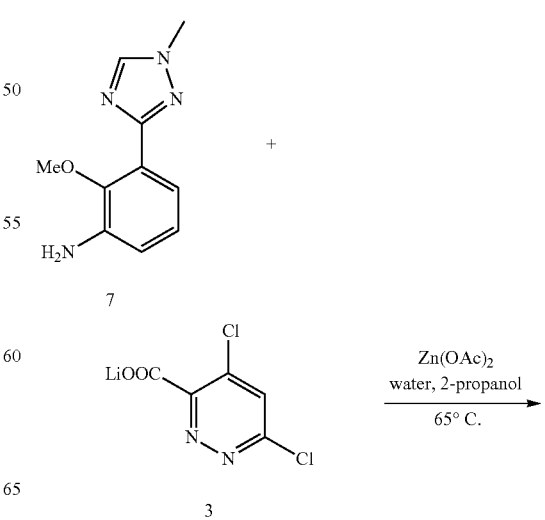

-continued

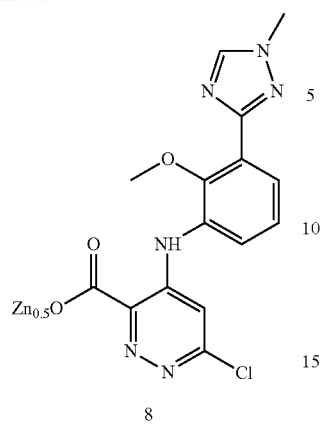

8

Water (6.0 kg, 6.0 L/kg) and Compound 7 (1.0 kg) were charged to a glass-lined reactor at 25° C. Zinc acetate dehydrate (1.08 kg, 1.0 equiv) was added, followed by Compound 3 (1.28 kg, 1.20 equiv). The reactor line was rinsed with 2-propanol (0.79 kg, 1.0 L/kg) and water (1.50 kg, 1.50 L/kg). The resulting homogeneous solution was heated to 65° C. and aged until the reaction reached completion. Water (7.0 kg, 7.0 L/kg) was added, and the crude mixture was cooled to 20° C. and aged for 30 min. The product was isolated by filtration. The crude solid was washed sequentially with water (6.0 kg, 6.0 L/kg), water (6.0 kg, 6.0 L/kg), THF (5.3 kg, 6.0 L/kg) and THF (5.3 kg, 6.0 L/kg). The cake was dried under vacuum at 70° C. Compound 8 was isolated in 98 AP and 94% yield.

Step 4: Preparation of Compound 9

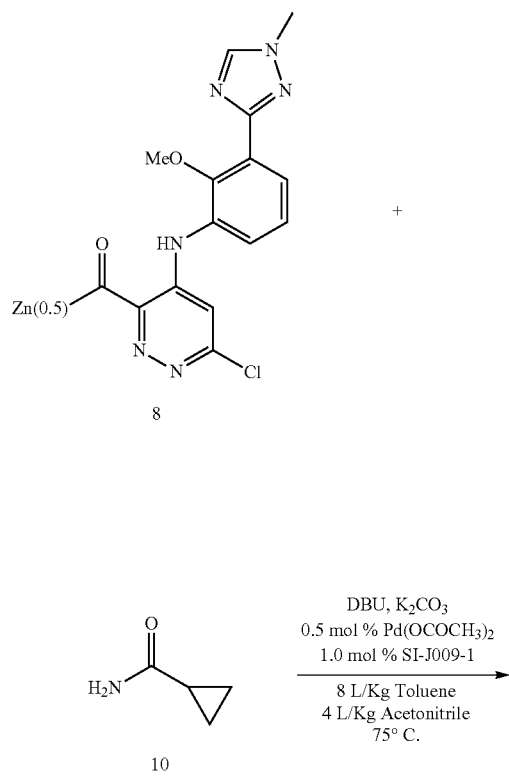

-continued

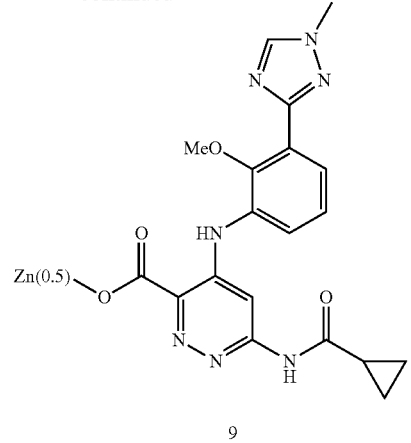

9

A separate glass-lined reactor was flushed with nitrogen. Toluene (0.87 kg, 1.0 L/kg) and MeCN (0.79 kg, 1.0 L/kg) were charged, followed by (2R)-1-[(1R)-1-[bis(1,1-dimethylethyl) phosphino] ethyl]-2-(dicyclohenxyphosphino) ferrocene (Josiphos SL-009-01) (14.1 g, 1.0 mol %) and palladium acetate (2.9 g, 0.5 mol %). The reactor line was rinsed with toluene (0.43 kg, 0.5 L/kg). The resulting pre-formed catalyst solution was kept under nitrogen until further usage.

At 20° C., toluene (3.46 Kg, 4.0 L/kg) and ACN (1.57 kg, 2.0 L/kg) were charged to a glass-lined reactor flushed with nitrogen. Compound 8 (1.00 kg) was added, followed by DBU (0.39 kg, 1.00 equiv). The reactor line was rinsed with toluene (0.43 kg, 0.5 L/kg). Compound 10 (0.54 kg, 2.5 equiv) and $K_2CO_3$ (325 mesh grade, 0.70 kg, 2.0 equiv) were added to the reaction mixture, followed by toluene (1.30 kg, 1.5 L/kg) and ACN (0.79 kg, 1.0 L/kg). The pre-formed catalyst solution was transferred into the reaction mixture, which was then heated to 75° C. and agitated until the reaction reached completion.

The reaction crude was cooled to 20° C. Aqueous acetic acid (50 Volume %, 4.0 kg, 4.0 L/kg) was charged slowly over the course of 1 h. Glacial acetic acid (10.5 kg, 10.0 L/kg) was then added. The resulting homogeneous solution was washed twice with heptane (2×3.42 kg, 2×5.0 L/kg). The bottom aqueous layer was collected and transferred to a clean reactor. Water (5.0 kg, 5.0 L/kg) was added, followed by Compound 9 seeds (0.01 kg, 1.0 wt %). The slurry was aged for 2 h at 20° C. Additional water (2.0 kg, 2.0 L/kg) was added, and the slurry was further aged for 6 h. The product was isolated by filtration. The crude cake was washed with aqueous ACN (50 Volume %, 4.5 kg, 5.0 L/kg) followed by ACN (3.9 kg, 5.0 L/kg). The cake was dried under vacuum at 65° C. Compound 9 was isolated in 98.5 AP and 84% yield.

Step 5: Preparation of the Compound (I)

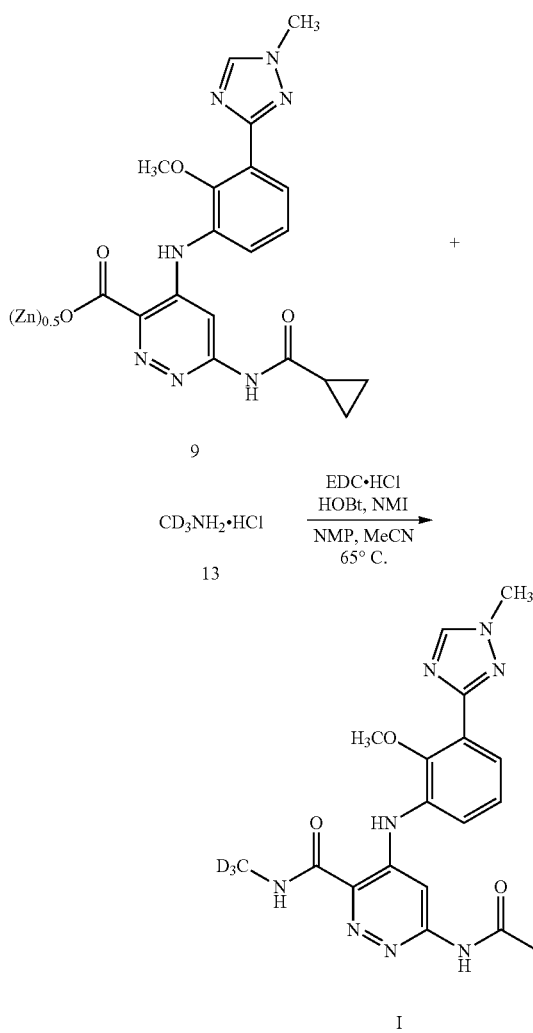

NMP (2.06 kg, 2.0 L/kg) and ACN (0.78 kg, 1.0 L/kg) were charged to a glass-lined reactor and agitated at 20° C. N-Methylimidazole (0.13 kg, 0.7 equiv.), Compound 13 (0.17 kg, 1.2 equiv.) and Compound 9 (1.00 kg) were charged to the reaction mixture. The mixture was heated to 65° C. and aged until homogeneous. HOBt 20% wet (0.17 kg, 0.5 eq), followed by EDC HCl (0.54 kg, 1.4 eq) were then charged to the reaction mixture. The reactor was rinsed with ACN (0.78 kg, 1.0 L/kg), then the resulting mixture was aged at 65° C. until the reaction reached completion. The reaction was quenched by charging water (1.0 kg, 1 L/kg), then diluted with ACN (3.0 kg, 3 L/kg). The reaction mixture was aged at 65° C. for 1 h, before cooling to 0° C., and aged for an additional 12 h at 0° C. The product was isolated by filtration. The wet cake was washed with 2:1 Water:ACN (2.8 kg, 3 L/kg) then ACN (2.4 kg, 3 L/kg), before drying under full vacuum at 65° C. Compound (I) was isolated in >99.5% purity and 91% yield.

NMP (6.2 kg, 6.0 L/kg) and Compound (I) (1.0 kg) were charged to a glass-lined reactor. The batch was heated to 70° C. to form a pale yellow solution, which was then transferred through a polish filter to a clean vessel at 70° C. 2-Propanol (2.4 kg, 3 L/kg) was added, followed by Compound I seeds (0.005 kg, 0.005 kg/kg). After aging for 1 h, additional 2-propanol (4.8 kg, 6 L/kg) was charged over the course of 2 h (3 L/kg/hr). The slurry was aged for 1 h at 70° C., cooled slowly to 0° C. and aged for additional 12 h at 0° C. Product was isolated by filtration. The wet cake was washed with 2-propanol (2×3.1 kg, 2×4 L/kg) before drying under full vacuum at 65° C. Compound (I) was isolated in >99.9% purity and 83% yield.

Preparation of Compound 7
Step 1: Preparation of N-methyl-N-formyl hydrazine

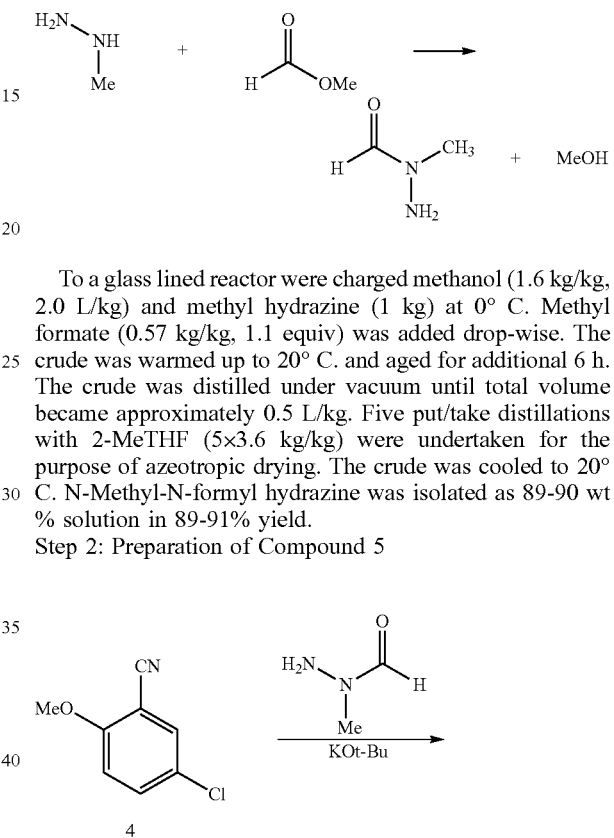

To a glass lined reactor were charged methanol (1.6 kg/kg, 2.0 L/kg) and methyl hydrazine (1 kg) at 0° C. Methyl formate (0.57 kg/kg, 1.1 equiv) was added drop-wise. The crude was warmed up to 20° C. and aged for additional 6 h. The crude was distilled under vacuum until total volume became approximately 0.5 L/kg. Five put/take distillations with 2-MeTHF (5×3.6 kg/kg) were undertaken for the purpose of azeotropic drying. The crude was cooled to 20° C. N-Methyl-N-formyl hydrazine was isolated as 89-90 wt % solution in 89-91% yield.

Step 2: Preparation of Compound 5

To a glass lined reactor were charged potassium tert-butoxide (1.5 kg/kg, 2.4 equiv) and THF (12.2 kg/kg) at 0° C. A mixture of Compound 4 (1.0 kg), N-methyl-N-formyl hydrazine (1.0 kg/kg, 2.30 equiv) and THF (5.3 kg/kg, 6.0 L/kg) was added slowly. The reactor line was rinsed with THF (0.5 kg/kg). The reaction crude was aged at 0° C. until reaction reached completion. Water (5.0 kg/kg) was added, and the resulting mixture was aged at 0° C. for 30 min, heated to 40° C. and aged for additional 30 min. The layers were separated and the aqueous layer was discarded. The organic layer was washed with brine (15 wt %, 5.7 kg/kg) before distilling under vacuum until total volume became approximately 5 L/kg. Four put/take distillations with ethyl acetate (4×10 L/kg) were undertaken for the purpose of azeotropic drying. The crude was cooled to 20° C. Sulfuric acid (0.66 kg/kg, 1.10 equiv.) was added, and the slurry was agitated for 2-3 h. Product was isolated by filtration. The cake was consecutively washed with ethyl acetate (2×6.5 L/kg) and heptane (8 L/kg), and dried under vacuum at 45° C. Compound 5 was isolated in 99 AP and 83% yield.

Step 3: Preparation of Compound 6

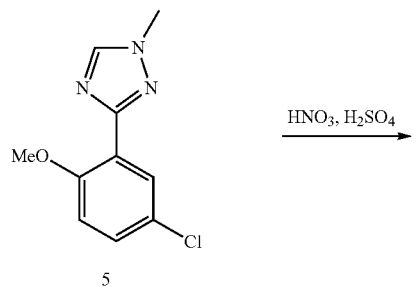

To a glass lined reactor were charged concentrated sulfuric acid (4.5 kg/kg) and Compound 5 (1.0 kg) at 0-5° C. Nitric acid (68 wt %, 0.35 kg/kg, 1.2 equiv) was added drop-wise. The mixture was agitated at 0-5° C. until reaction reached completion.

In a separate reactor, water (12 kg/kg) and methanol (6.5 kg/kg, 8.3 L/kg) were mixed well at 20° C. The nitration crude was transferred slowly into the methanol water mixture. The reactor line was rinsed with methanol (0.5 kg/kg). The crude was heated to 40-45° C. Aqueous ammonium hydroxide (25 wt %, 7.4 kg/kg) was added slowly. The resulting slurry was cooled to 20° C. and agitated for 3 h. Product was isolated by filtration. The cake was washed with water (2×6 L/kg), and dried under vacuum at 45° C. Compound 6 was isolated in 99 AP and 95% yield.

Step 4: Preparation of Compound 7

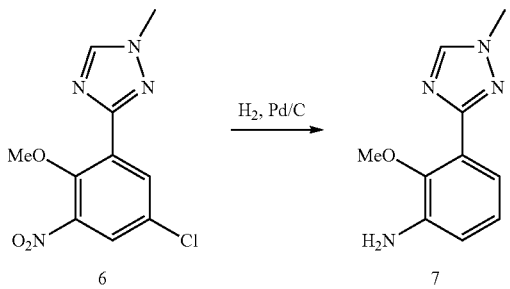 [SMILES: COc1c(-c2ncn(C)n2)cc(Cl)cc1[N+](=O)[O-] ; COc1c(N)cccc1-c1ncn(C)n1]

To a high pressure reactor flushed with nitrogen were charged methanol (8.0 kg/kg) and Compound 6 (1.0 kg). With careful exclusion of oxygen, sodium bicarbonate (0.6 kg/kg, 2.0 equiv.) and Pd/C (10% loading, 50% wet, 0.02 kg/kg) were added. The reactor was pressurized with hydrogen (41-46 psi), and the reaction mixture was aged at 20° C. for 6 h then heated to 45° C. and aged till reaction reached completion. The reactor was flushed with nitrogen, and the reaction crude was filtered to remove Pd/C. Methanol (5 kg/kg) was used to aid the transfer. The combined filtrates were distilled under vacuum until total volume became approximately 2.5 L/kg. Water (10 kg/kg) was added, and the crude was distilled under vacuum until total volume became approximately 2.5 L/kg. The crude was heated to 70° C. Brine (25 wt %, 9.0 kg/kg) was added, and the resulting crude was agitated for 6 h at 70° C. After cooling down to 0° C., the crude was further aged for 6 h. Product was isolated by filtration. The cake was washed with brine (pre-cooled to 0° C., 25 wt %, 2.0 kg/kg), and dried under vacuum at 45° C. Compound 7 was isolated in 99 AP and 88% yield.

Preparation of Compound 13

Step 1: Preparation of Compound 11 and Compound 12

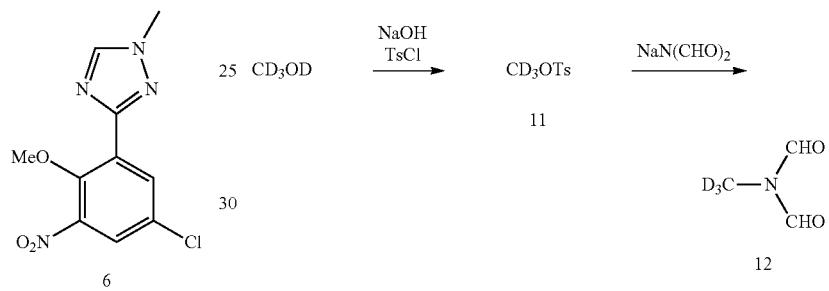

To a glass lined reactor flushed with nitrogen were charged water (16.3 L/kg) and sodium hydroxide (3.3 kg, 3.0 equiv). The mixture was aged till sodium hydroxide reached full dissolution. The crude was cooled to 0° C. d$_4$-Methanol (1.0 kg) and THF (4.5 L/kg) were charged. A solution of TsCl (6.3 kg, 1.2 equiv) in THF (6.3 kg, 7.1 L/kg) was added over the course of 2 h. The crude was agitated at 0° C. until reaction reached completion. The batch was warmed to 20° C. The layers were separated. The collected organic layer was diluted with MTBE (4.0 kg, 5.4 L/kg), washed with brine twice (25 wt %, 4.0 kg followed by 12 kg). The organic layer was distilled under vacuum until total volume became approximately 10 L/kg. Two put/take distillations with ACN (2×10 L/kg) were undertaken for the purpose of azeotropic drying. The crude was cooled to 20° C. ACN (10.0 kg, 12.8 L/kg) and NaN(CHO)$_2$ (3.3 kg, 1.2 equiv.) were added. The crude was heated to 65° C. and agitated until reaction reached completion. After cooling down to 5° C., the mixture was filtered, and the crude cake was washed with ACN twice (2×2.5 kg, 2×3.2 L/kg). The combined filtrates were distilled under vacuum until total volume became approximately 3 L/kg. The crude was cooled to 20° C. Compound 12 was isolated as an oil with 80-85 wt % in 60-70% yield.

Step 2: Preparation of Compound 13

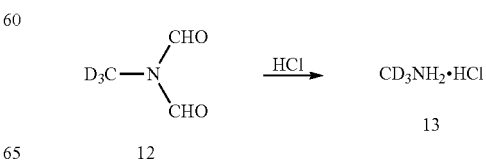

To a glass lined reactor were charged Compound 12 (1.0 kg) and methanol (3.9 kg, 5.0 L/kg) at 20° C. A solution of HCl in IPA (5-6 Normal, 4.5 kg, 1.5 equiv) was added. The resulting mixture was heated to 50° C. and agitated until reaction reached completion. THF (10 kg, 11.2 L/kg) was added slowly and the crude was cooled to 0° C. over 2 h to afford a slurry. The product was isolated by filtration. The cake was washed with THF (3.7 kg, 4.1 L/kg), and dried under vacuum at 45° C. Compound 13 was isolated in 80% yield.

Optional Recrystallization of Compound 13:

Methanol (5.6 kg, 8.3 L/kg) and Compound 13 (1.0 kg) were charged to a glass-lined reactor. DBU (0.1 kg) was added slowly. The crude was agitated for 1 h. THF (12.4 kg, 13.9 L/kg) was added slowly, and the resulting slurry was aged for 2 h. The product was isolated by filtration. The cake was washed with THF (2.6 kg, 2.9 L/kg), and dried under vacuum at 45° C. Compound 13 was isolated in 60% yield ($1^{st}$ crop). The mother liquor was distilled under vacuum until total volume became approximately 1 L/kg. Two put/take distillations with methanol (2×2.8 kg, 2×3.6 L/kg) were performed and the solution was concentrated back to ~1 L/kg. The crude was cooled to 20° C. THF (4.8 kg, 5.4 L/kg) was added, and the resulting slurry was aged for 2 h. The product was isolated by filtration. The cake was washed with THF (1.0 kg), and dried under vacuum at 45° C. Compound 13 was isolated in 25% yield ($2^{nd}$ crop).

1. Single Crystal X-Ray Measurements

Single crystal X-ray data were collected using a Bruker D8 Venture diffractometer equipped with a Photon III detector and IµS microfocus X-ray source of monochromatic Cu Kα radiation. The single crystals were at 100 K during data collection.

Indexing and processing of the measured intensity data were carried out with the APEX3 program suite (Bruker AXS, Inc., 5465 East Cheryl Parkway, Madison, WI 53711 USA).

The final unit cell parameters were determined using the full data set. The structures were solved by direct methods and refined by full-matrix least-squares approach using the SHELXTL software package (G. M. Sheldrick, SHELXTL v6.14, Bruker AXS, Madison, WI USA.). Structure refinements involved minimization of the function defined by $\Sigma w(|F_o|-|F_c|)^2$, where w is an appropriate weighting factor based on errors in the observed intensities, $F_o$ is the structure factor based on measured reflections, and $F_c$ is the structure factor based on calculated reflections. Agreement between the refined crystal structure model and the experimental X-ray diffraction data is assessed by using the residual factors $R=\Sigma||F_o|-|F_c||/\Sigma|F_o|$ and $wR=[\Sigma w(|F_o|-|F_c|)^2/\Sigma w|F_o|]^{1/2}$. Difference Fourier maps were examined at all stages of refinement. All non-hydrogen atoms were refined with anisotropic thermal displacement parameters. Hydrogen and deuterium atoms on carbon atoms were introduced using idealized geometry with isotropic temperature factors and included in structure factor calculations with fixed parameters. Hydrogen atoms on heteroatoms were located from the residual electron density and freely refined with isotropic displacement parameters.

2. Powder X-Ray Diffraction

XRD data were collected using a Bruker D8 Discover DaVinci with XYZ Stage. The IµS X-ray generator was operated at 50 kV and 1 mA with a Cu target (CuKα radiation). Incident beam optics included Montel mirrors with a 0.3 mm collimator. Photons were counted using an Eiger2 R 500K Detector in 2D, 2θ optimized mode. Sample-to-detector distance was set to 140 mm. The samples were run for 100 seconds in transmission, snapshot mode with the incident beam at 0° and the detector at 17.5°.

3. Differential Scanning Calorimetry

Differential scanning calorimetry (DSC) experiments were performed using a TA Instrument—model Q2000. The sample (about 1-10 mg) was weighed in an aluminum pan and the weight recorded accurately to a hundredth of a milligram before transferring the sample to the DSC. The instrument was purged with nitrogen gas at 50 mL/min. Data were collected between room temperature and 300° C. at a heating rate of 10° C./min. DSC plots were generated such that the endothermic peaks pointed down.

4. Thermal Gravimetric Analysis

Thermal gravimetric analysis (TGA) experiments were performed using a TA Instrument—model Q5000. The sample (about 10-30 mg) was placed in a previously tarred platinum pan. The weight of the sample was measured accurately and recorded to a thousandth of a milligram by the instrument. The furnace was purged with nitrogen gas at 25 mL/min. Data were collected between room temperature and 300° C. at a heating rate of 10° C./min.

5. Moisture Sorption Isotherms

Moisture sorption isotherms were collected in a TA Instrument VTI-SA+ Vapor Sorption Analyzer using approximately 10 mg of sample. The sample was dried at 60° C. until the loss rate of 0.005 wt %/min was obtained for 10 minutes. The sample was tested at 25° C. and 4 or 5, 15, 25, 35, 45, 50, 65, 75, 85, and 95% RH (relative humidity). Equilibration at each RH was reached when the rate of 0.01 wt %/min for 35 minutes was achieved or a maximum of 600 minutes was reached.

What is claimed is:

1. Crystalline Form E of 6-(cyclopropanecarboxamido)-4-((2-methoxy-3-(1-methyl-1H-1,2,4-triazol-3-yl)phenyl)amino)-N-(methyl-d$_3$)pyridazine-3-carboxamide.

2. The crystalline form according to claim 1 characterized by at least one of the following:
   (i) unit cell parameters equal to the following:
      a=10.41±0.10 Å
      b=12.65±0.10 Å
      c=15.70±0.10 Å
      α=90.0°
      β=103.5±1.0°
      γ=90.0°
      Space group: P2$_1$/n
      Molecules per unit cell (Z): 4,
   wherein the unit cell parameters of Form E of 6-(cyclopropanecarboxamido)-4-((2-methoxy-3-(1-methyl-1H-1,2,4-triazol-3-yl)phenyl) amino)-N-(methyl-d$_3$) pyridazine-3-carboxamide are measured at a temperature of about 100 K;
   (ii) a powder X-ray diffraction pattern comprising two or more 2θ values in degrees (CuKα) selected from: 9.0±0.2, 11.3±0.2, 15.2±0.2, and 21.1±0.2, wherein the PXRD pattern is measured at room temperature;
   (iii) an observed powder X-ray diffraction pattern as shown in FIG. 1, wherein the PXRD pattern is measured at room temperature; or
   (iv) an endotherm with peak max in the range of from about 249° ° C. to about 253° C.

3. The crystalline form according to claim 1 characterized by a powder X-ray diffraction (PXRD) pattern comprising three or more 2θ values in degrees (CuKα) selected from: 9.0±0.2, 11.3±0.2, 15.2±0.2, and 21.1±0.2, wherein the PXRD pattern of the crystalline form is measured at room temperature.

4. The crystalline form according to claim 1 characterized by a powder X-ray diffraction pattern comprising the 2θ values in degrees (CuKα) at 9.0±0.2, 11.3±0.2, 15.2±0.2, and 21.1±0.2, wherein the PXRD pattern of the crystalline form is measured at room temperature.

5. The crystalline form according to claim 1 characterized by: (i) a powder X-ray diffraction pattern comprising the 2θ values in degrees (CuKα) at 9.0±0.2 and 11.3±0.2, measured at room temperature; and (ii) an endotherm with peak max in the range of from about 249° ° C. to about 253° C.

6. The crystalline form according to claim 1 characterized by: (i) a powder X-ray diffraction pattern comprising the 2θ values in degrees (CuKα) at 9.0±0.2, 11.3±0.2, 15.2±0.2, and 21.1±0.2, measured at room temperature; and (ii) an endotherm with peak max in the range of from about 249° C. to about 253° C.

7. The crystalline form according to claim 1 characterized by: (i) a powder X-ray diffraction pattern comprising the 2θ values in degrees (CuKα) at 9.0±0.2 and 11.3±0.2, measured at room temperature; and (ii) a differential scanning calorimetry (DSC) thermogram as shown in FIG. 2.

8. The crystalline form according to claim 1 characterized by: (i) a powder X-ray diffraction pattern comprising the 2θ values in degrees (CuKα) at 9.0±0.2, 11.3±0.2, 15.2±0.2, and 21.1±0.2, measured at room temperature; and (ii) a differential scanning calorimetry (DSC) thermogram as shown in FIG. 2.

9. The crystalline form according to claim 1 characterized by a mass increase of less than about 0.1% when subjected to an increase in relative humidity from about 5% to about 95%.

10. The crystalline form according to claim 1 characterized by a thermal gravimetric analysis plot comprising a mass loss of less than about 0.1% when heated from about 30° C. to about 150° C.

11. The crystalline form according to claim 1 wherein said Form E is in substantially pure form.

12. The crystalline form according to claim 1 characterized by an observed powder X-ray diffraction pattern as shown in FIG. 1.

13. A composition comprising 6-(cyclopropanecarboxamido)-4-((2-methoxy-3-(1-methyl-1H-1,2,4-triazol-3-yl)phenyl) amino)-N-(methyl-d$_3$)pyridazine-3-carboxamide, wherein at least 90 weight % of said 6-(cyclopropanecarboxamido)-4-((2-methoxy-3-(1-methyl-1H-1,2,4-triazol-3-yl)phenyl) amino)-N-(methyl-d$_3$)pyridazine-3-carboxamide is in crystalline Form E.

14. The composition according to claim 13, wherein at least 95 weight % of said 6-(cyclopropanecarboxamido)-4-((2-methoxy-3-(1-methyl-1H-1,2,4-triazol-3-yl)phenyl) amino)-N-(methyl-d$_3$)pyridazine-3-carboxamide is in crystalline Form E.

15. A composition comprising crystalline 6-(cyclopropanecarboxamido)-4-((2-methoxy-3-(1-methyl-1H-1,2,4-triazol-3-yl)phenyl) amino)-N-(methyl-d$_3$)pyridazine-3-carboxamide, wherein at least 95 weight % of said crystalline 6-(cyclopropanecarboxamido)-4-((2-methoxy-3-(1-methyl-1H-1,2,4-triazol-3-yl)phenyl) amino)-N-(methyl-d$_3$)pyridazine-3-carboxamide is crystalline Form E.

16. A composition comprising 6-(cyclopropanecarboxamido)-4-((2-methoxy-3-(1-methyl-1H-1,2,4-triazol-3-yl)phenyl) amino)-N-(methyl-d$_3$)pyridazine-3-carboxamide, wherein said 6-(cyclopropanecarboxamido)-4-((2-methoxy-3-(1-methyl-1H-1,2,4-triazol-3-yl)phenyl) amino)-N-(methyl-d$_3$)pyridazine-3-carboxamide consists essentially of crystalline Form E.

17. A pharmaceutical composition comprising the crystalline form according to claim 1 and a pharmaceutically acceptable carrier or diluent.

18. A pharmaceutical composition comprising crystalline Form E of 6-(cyclopropanecarboxamido)-4-((2-methoxy-3-(1-methyl-1H-1,2,4-triazol-3-yl)phenyl) amino)-N-(methyl-d$_3$)pyridazine-3-carboxamide and a pharmaceutically acceptable carrier or diluent, wherein said crystalline Form E is characterized by a powder X-ray diffraction pattern comprising 2θ values in degrees (CuKα) at 9.0±0.2 and 11.3±0.2, when measured at room temperature.

* * * * *